(12) United States Patent
Lin

(10) Patent No.: US 8,574,868 B2
(45) Date of Patent: Nov. 5, 2013

(54) METHOD FOR DEPARAFFINIZING FORMALIN-FIXED PARAFFIN-EMBEDDED TISSUE

(75) Inventor: Shang-Chi Lin, Tainan County (TW)

(73) Assignee: Industrial Technology Research Institute, Hsinchu (TW)

( * ) Notice: Subject to any disclaimer, the term of this patent is extended or adjusted under 35 U.S.C. 154(b) by 351 days.

(21) Appl. No.: 12/979,979

(22) Filed: Dec. 28, 2010

(65) Prior Publication Data

US 2012/0129251 A1    May 24, 2012

(30) Foreign Application Priority Data

Nov. 24, 2010 (TW) .............................. 99140497 A

(51) Int. Cl.
*G01N 1/30* (2006.01)
(52) U.S. Cl.
USPC ....................................................... 435/40.52
(58) Field of Classification Search
None
See application file for complete search history.

(56) References Cited

U.S. PATENT DOCUMENTS

| | | | |
|---|---|---|---|
| 4,659,498 A * | 4/1987 | Stoufer | ............................ 134/40 |
| 6,090,935 A | 7/2000 | Breivik et al. | |
| 6,183,995 B1 | 2/2001 | Burmer et al. | |
| 6,248,535 B1 | 6/2001 | Danenberg et al. | |
| 6,428,936 B1 | 8/2002 | Schenker | |
| 6,610,488 B2 | 8/2003 | Danenberg et al. | |
| 7,364,846 B2 | 4/2008 | Erlander et al. | |
| 7,544,471 B2 | 6/2009 | Wang et al. | |
| 2002/0009795 A1 | 1/2002 | Danenberg et al. | |
| 2004/0091910 A1 | 5/2004 | Danenberg et al. | |
| 2005/0042656 A1 | 2/2005 | Davis et al. | |
| 2006/0199197 A1 | 9/2006 | Danenberg et al. | |
| 2007/0026411 A1 | 2/2007 | Wang et al. | |
| 2007/0026432 A1 | 2/2007 | Ke et al. | |
| 2007/0128634 A1 | 6/2007 | Ke et al. | |
| 2009/0035761 A1 | 2/2009 | Danenberg et al. | |
| 2009/0092979 A1 | 4/2009 | Danenberg | |
| 2009/0202998 A1 | 8/2009 | Schlumpberger et al. | |
| 2009/0264641 A1 | 10/2009 | Rosell Costa et al. | |

FOREIGN PATENT DOCUMENTS

TW    I-2776952    4/2007

OTHER PUBLICATIONS

Fredricks, D.N. and Relman, D.A., "Paraffin Removal from Tissue Sections for Digestion and PCR Analysis" (1999) BioTechniques, vol. 26, 198-199.*
Thomas, G.A. and Erskine Hawkins, J., "Physical and Thermodynamic Properties of Terpenes. IV. The Dielectric Constant, Refractive Index and Density of Some Terpenes" (1954) J. Am. Chem. Soc., vol. 76, 4856-4858.*
The Merck Index—An Encyclopedia of Chemicals, Drugs, and Biologicals, 14th Ed., O'Neal, M.J., Heckelman, P.E., Koch, C.B., Roman, K.J., Kenny, C.M., and D'Arecca, M.R., Eds.; Merck & Co., Inc.: Whitehouse Station, NJ, 2006.*
Nishiguchi, M.K., Doukakis, P., Egan, M., Kizirian, D., Phillips, A., Prendini, L., Rosenbaum, H.C., Torres, E., Wyner, Y., DeSalle, R., and Giribet, G. "DNA Isolation Procedures" In Techniques in Molecular Systematics and Evolution, Chapter 12, DeSalle, R., Giribet, G., and Wheeler, W., Eds.; Birkhauser Verlag: Basel, Switzerland, 2002, 249-287.*
Taiwanese Office Action dated Jun. 26, 2013.

* cited by examiner

*Primary Examiner* — Allison Ford
*Assistant Examiner* — Michelle F. Paguio Frising
(74) *Attorney, Agent, or Firm* — Muncy, Geissler, Olds & Lowe, PLLC

(57) ABSTRACT

The invention provides a method for deparaffinizing a formalin-fixed paraffin-embedded tissue, including: providing a formalin-fixed paraffin-embedded tissue sample; mixing the formalin-fixed paraffin-embedded tissue sample with an organic solvent and water or with an organic solvent and an aqueous solution to form a mixture, wherein a density of the organic solvent is less than that of the water or the aqueous solution, and the organic solvent is immiscible with the water or the aqueous solution; and separating the mixture into an organic solution layer and an aqueous solution layer, wherein a paraffin dissolved from the formalin-fixed paraffin-embedded tissue sample is in the organic solution layer and a deparaffinized tissue from the formalin-fixed paraffin-embedded tissue sample is in the aqueous solution layer and/or an interlayer between the organic solution layer and the aqueous solution layer.

12 Claims, 2 Drawing Sheets

METHOD FOR DEPARAFFINIZING FORMALIN-FIXED PARAFFIN-EMBEDDED TISSUE

CROSS REFERENCE TO RELATED APPLICATIONS

This Application claims priority of Taiwan Patent Application No. 099140497, filed on Nov. 24, 2010, the entirety of which is incorporated by reference herein.

BACKGROUND

1. Technical Field

The disclosure relates to a method for deparaffinizing a formalin-fixed paraffin-embedded tissue, and in particular relates to a method for deparaffinizing a formalin-fixed paraffin-embedded tissue, wherein a step of repeatedly washing the sample with ethanol or an aqueous solution thereof, is not required.

2. Description of the Related Art

In recent years, due to the development of gene detection techniques, it is now possible to interpret the developmental stages of cancer in tumor cells from gene expression profiles of a tumor of a patient. Because, generally, hospitals preserve samples using the formalin-fixed paraffin-embedded (FFPE) technique, FFPE samples are the most convenient type of samples which can be obtained.

At present, a number of techniques for extracting nucleic acid from a formalin-fixed paraffin-embedded sample have been disclosed. However, all of them need complicated and time consuming deparaffinizing steps, such as, washing of a paraffin-containing sample with xylene, and then repeatedly washing the sample with ethanol or an aqueous solution thereof, to wash out the xylene from the sample, so that a subsequently needed water soluble reagent will be able to permeate into and react with the tissues in the sample more completely. The step of washing the sample with ethanol to increase the hydrophilism of tissues in the sample is called rehydration process.

Another deficiency with the conventional steps, is that some clinical samples, such as core needle biopsy FFPE samples, only have a trace of the sample therein. Thus, when the sample is washed with xylene, most of the paraffin slice tissue from the sample in xylene would appear transparent. However, after a high speed centrifugal process, the tissues of the sample, deparaffinized by the xylene, form a transparent precipitation at a bottom of a tube, which eventually loosens and easily floats around. Thus, even if the xylene is carefully removed, it is not guaranteed, that the tissues of the sample will not be removed together with the xylene. Therefore, presently, a new method is needed for deparaffinizing a formalin-fixed paraffin-embedded tissue to overcome the problems mention above.

SUMMARY

The disclosed provides a method for deparaffinizing a formalin-fixed paraffin-embedded tissue, including: providing a formalin-fixed paraffin-embedded tissue sample; mixing the formalin-fixed paraffin-embedded tissue sample with an organic solvent and water or with an organic solvent and an aqueous solution to form a mixture, wherein a density of the organic solvent is less than that of the water or the aqueous solution, and the organic solvent is immiscible with the water or the aqueous solution; and separating the mixture into an organic solution layer and an aqueous solution layer, wherein a paraffin dissolved from the formalin-fixed paraffin-embedded tissue sample is in the organic solution layer and a deparaffinized tissue from the formalin-fixed paraffin-embedded tissue sample is in the aqueous solution layer and/or an interlayer between the organic solution layer and the aqueous solution layer.

The disclosure further provides a kit for the method for deparaffinizing the formalin-fixed paraffin-embedded tissue mentioned above, comprising: an organic solvent; and water or an aqueous solution, wherein a density of the organic solvent is less than that of the water or the aqueous solution, and the organic solvent is immiscible with the water or the aqueous solution.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION

Figure 1:
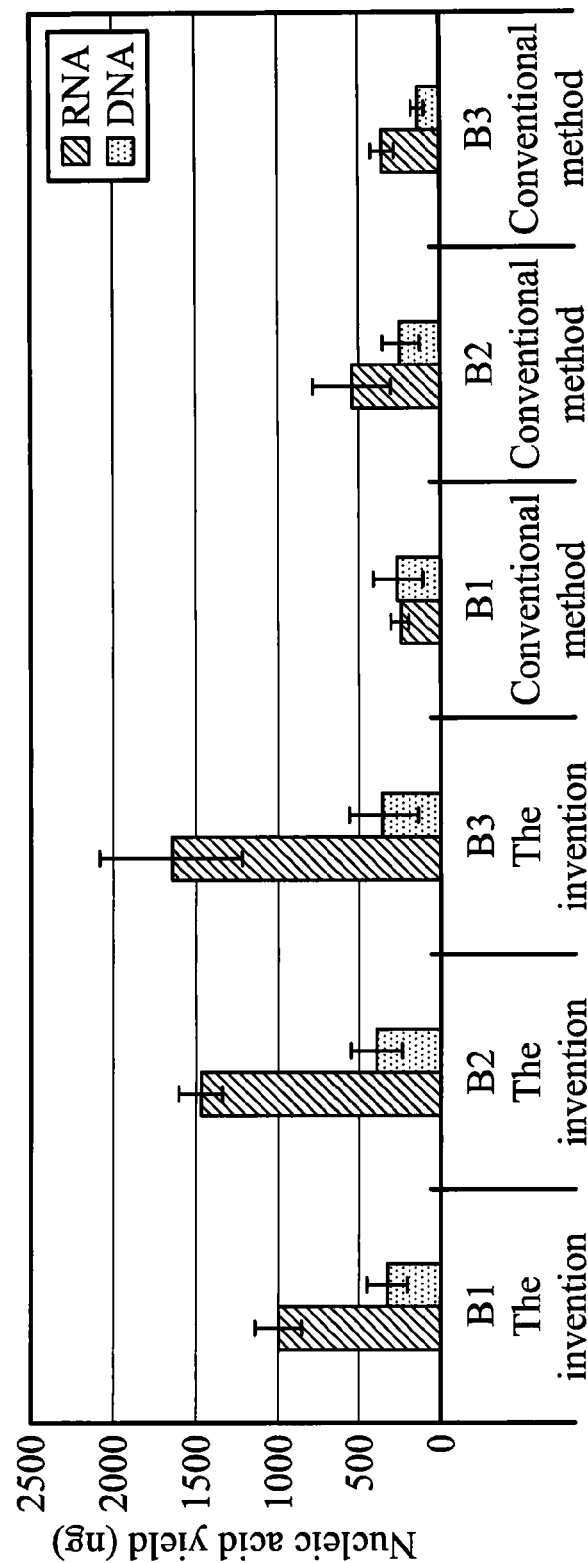
FIG. 1 shows nucleic acid yields obtained by using a conventional deparaffinizing method and the deparaffinizing method of the invention, respectively.

The following description is of the best-contemplated mode of carrying out the invention. This description is made for the purpose of illustrating the general principles of the invention and should not be taken in a limiting sense. The scope of the invention is best determined by reference to the appended claims.

In order to solve the problems of sample losing and time consuming due to repeatedly washing a tissue sample with ethanol or the aqueous solution thereof to remove the organic solvent used for dissolving the paraffin, remained on the tissue sample, in one aspect of the invention, the disclosed provides a method for deparaffinizing a formalin-fixed paraffin-embedded tissue, wherein the step of repeatedly washing a tissue sample with ethanol or the aqueous solution thereof is not required. The method may comprise the steps as following.

First, a formalin-fixed paraffin-embedded tissue sample is provided. Then, the formalin-fixed paraffin-embedded tissue (FFPE) sample is mixed with an organic solvent and water or with an organic solvent and an aqueous solution to form a mixture, wherein a density of the organic solvent is less than that of the water or the aqueous solution, and the organic solvent is immiscible with the water or the aqueous solution.

The order for adding the organic solvent and the water or the order for adding the organic solvent and the aqueous solution is not particularly limited. In one embodiment, the organic solvent may be added to the formalin-fixed paraffin-embedded tissue sample first, and then the water or the aqueous solution is added thereto and well mixed with the formalin-fixed paraffin-embedded tissue sample and the organic solvent to form a mixture. In another embodiment, the water or the aqueous solution may be added to the formalin-fixed paraffin-embedded tissue sample first, and then the organic solvent is added thereto and well mixed with the formalin-fixed paraffin-embedded tissue sample and the water or the aqueous solution to form a mixture. In further another embodiment, the organic solvent and the water may be added to the formalin-fixed paraffin-embedded tissue, simultaneously, or the organic solvent and the aqueous solution may be added to the formalin-fixed paraffin-embedded tissue, simultaneously, and mixed with the formalin-fixed paraffin-embedded tissue to form a mixture.

A pH value of the mixture is not particularly limited. In one embodiment, taking into account the subsequent steps of extracting nucleic acid from the sample after deparaffinizing the sample, the pH value of the mixture may be maintained at about pH 6-8.

The organic solvent mentioned above with density is less than that of the water or the aqueous solution and which are immiscible with the water or the aqueous solution is used for dissolving the paraffin out from the formalin-fixed paraffin-embedded tissue sample, and the water or the aqueous solution is used to divide a tissues sample of the formalin-fixed paraffin-embedded tissue sample from the paraffin after the paraffin is dissolved out from the formalin-fixed paraffin-embedded tissue. In one embodiment, examples of the organic solvent with density less than that of the water or the aqueous solution and which are immiscible with the water or the aqueous solution are described in U.S. Pat. No. 6,632,598, such as a non-polar hydrocarbon or a mixture of hydrocarbons. The foregoing organic solvent which is conventionally used comprises an alkylbenzene of aromatic hydrocarbon, such as xylene or toluene. The foregoing organic solvent may further comprise an aliphatic hydrocarbon, a terpene (such as 2,6-dimethyl-2,4,6-octatriene (Allo-ocimene)), a petroleum distillate and an isoparaffinic hydrocarbon. The examples of water may comprise, but is not limited to, distilled water, deionized water or RNase-free water. Moreover, content of the aqueous solution which is immiscible with the organic solvent may comprise water and other ingredients. The other ingredients may be optionally selected. For example, taking into account the subsequent steps of extracting nucleic acid from the sample after deparaffinizing the sample, the other ingredients may comprise such as Tris-HCl and/or EDTA, etc., but is not limited thereto. Furthermore, water of the content of the aqueous solution may comprise distilled water, deionized water or RNase-free water, but is not limited thereto.

In addition, the ratio of the formalin-fixed paraffin-embedded tissue sample to the organic solvent is not particularly limited; however, the amount of the organic solvent must be enough to dissolve the paraffin contained in the formalin-fixed paraffin-embedded tissue sample. In one embodiment, the only requirement for the amount of the organic solvent, is that it is enough to cover the formalin-fixed paraffin-embedded tissue sample.

Next, after the formalin-fixed paraffin-embedded tissue sample is mixed with the organic solvent and the water or with the organic solvent and the aqueous solution to form the mixture, the mixture is separated into an organic solution layer and an aqueous solution layer, wherein a paraffin dissolved from the formalin-fixed paraffin-embedded tissue sample is in the organic solution layer and a deparaffinized tissue from the formalin-fixed paraffin-embedded tissue sample is in the aqueous solution layer and/or an interlayer between the organic solution layer and the aqueous solution layer. Hence, completing the deparaffinization steps of the formalin-fixed paraffin-embedded tissue sample.

Since the densities of the organic solvent and the water or the densities of the organic solvent and the aqueous solution are different, the mixture mentioned above is separated into an organic solution layer and an aqueous solution layer, naturally. In one embodiment, a method for separating the mixture into the organic solution layer and the aqueous solution layer may comprise, but is not limited to, performing a centrifugal process to the mixture.

In one embodiment, the aqueous solution layer and/or the interlayer between the organic solution layer and the aqueous solution layer mentioned above may be further used in a nucleic acid extraction process. In one embodiment, the nucleic acid extraction process may comprise adding a digestion buffer and a proteinase to the aqueous solution layer and/or the interlayer between the organic solution layer and the aqueous solution layer. Examples of the proteinase may comprise a proteinase K.

In one embodiment, the method for deparaffinizing a formalin-fixed paraffin-embedded tissue may further comprise a step of removing the organic solution layer after separating the mixture into the organic solution layer and the aqueous solution layer.

Moreover, in another embodiment, after removing the organic solution layer, the organic solvent may be added into the aqueous solution layer again, and the organic solvent and the aqueous solution layer are mixed to form a second mixture. After that, the second mixture is separated into a second organic solution layer and a second aqueous solution layer.

The second aqueous solution layer and/or a second interlayer between the second organic solution layer and the second aqueous solution layer mentioned above may be further used in a nucleic acid extraction process.

Since the densities of the organic solvent and the water or the densities of the organic solvent and the aqueous solution are different, the second mixture mentioned above is separated into the second organic solution layer and the second aqueous solution layer, naturally. In one embodiment, a method for separating the second mixture into the second organic solution layer and the second aqueous solution layer may comprise, but is not limited to, performing a centrifugal process to the second mixture.

In one embodiment, the method for deparaffinizing a formalin-fixed paraffin-embedded tissue may further comprise a step of removing the second organic solution layer after separating the second mixture into the second organic solution layer and the second aqueous solution layer.

According to the foregoing, in another aspect of the invention, the disclosed may further provide a kit which is used in the method for deparaffinizing a formalin-fixed paraffin-embedded tissue of the invention. In one embodiment, the kit may comprise an organic solvent and water or may comprise an organic solvent and an aqueous solution, but is not limited thereto, wherein a density of the organic solvent is less than that of the water or the aqueous solution, and the organic solvent is immiscible with the water or the aqueous solution.

The organic solvent mentioned above with density is less than that of the water or the aqueous solution and which are immiscible with the water or the aqueous solution is used for dissolving the paraffin out from the formalin-fixed paraffin-embedded tissue sample, and the water or the aqueous solution is used to divide a tissues sample of the formalin-fixed paraffin-embedded tissue sample from the paraffin after the paraffin is dissolved out from the formalin-fixed paraffin-embedded tissue. In one embodiment, examples of the organic solvent with density less than that of the water or the aqueous solution and which are immiscible with the water or the aqueous solution are described in U.S. Pat. No. 6,632,598, such as a non-polar hydrocarbon or a mixture of hydrocarbons. The foregoing organic solvent which is conventionally used comprises an alkylbenzene of aromatic hydrocarbon, such as xylene or toluene. The foregoing organic solvent may further comprise an aliphatic hydrocarbon, a terpene (such as 2,6-dimethyl-2,4,6-octatriene (Allo-ocimene)), a petroleum distillate and an isoparaffinic hydrocarbon. The examples of water may comprise, but is not limited to, distilled water, deionized water or RNase-free water. Moreover, content of the aqueous solution which is immiscible with the organic solvent may comprise water and other ingredients. The other ingredients may be optionally selected. For example, taking into account the subsequent steps of extracting nucleic acid from the sample after deparaffinizing the sample, the other ingredients may comprise such as Tris-HCl and/or EDTA, etc., but is not limited thereto. Furthermore, water of the content of the aqueous solution may comprise distilled water, deionized water or RNase-free water, but is not limited thereto.

In addition, in another embodiment, the kit mentioned above may further comprise a reagent which is required in the step of extracting nucleic acid from the sample. In one embodiment, the kit mentioned above may further comprise a digestion buffer and a proteinase which are used in the step of extracting nucleic acid from the sample. Examples of the proteinase may comprise a proteinase K.

EXAMPLE

Example 1

Deparaffinization:

A slice of a formalin-fixed paraffin-embedded lung cancer tissue biopsy sample (tissue area: about 1 $cm^2$; thickness: 10 μm) was placed into a microcentrifuge tube. 600 μl of 100% xylene was added into the microcentrifuge tube and mixed with the sample by vortexing for 10 seconds to form a mixture. The mixture was centrifuged to be at the bottom of the microcentrifuge tube. Then, 194 μl of RNase-free water was added into the microcentrifuge tube, and the microcentrifuge tube was placed under a temperature of 50 for shaking horizontally for 3 minutes. The microcentrifuge tube was centrifuged at 12000 rpm for 3 minutes. Next, 550 μl of an upper layer liquid in the microcentrifuge tube was removed. After that, 600 μl of 100% xylene was added into the microcentrifuge tube again and mixed with the remaining liquid by vortexing for 10 seconds to form a mixture. The microcentrifuge tube was centrifuged at 12000 rpm for 3 minutes. Finally, 600 μl of an upper layer liquid in the microcentrifuge tube was removed to leave a lower liquid containing a deparaffinized tissue.

RNA Extraction

16 μl of a digestion buffer (6.3 μl of 1M Tris-HCl, pH 8.0+4.2 μl of 0.5 M EDTA, pH 8.0+5.5 μl of 20% SDS) and 8 μl of proteinase K [Qiagen #19131] were added into the microcentrifuge tube mentioned above which contained the lower liquid containing the deparaffinized tissue and mixed with the lower liquid to form a mixture. The microcentrifuge tube was placed under a temperature of 50 for shaking horizontally at 80 rpm for 3 hours. 70 μl of a FARB buffer [Favorgen cat#FABRK 001-1] and 300 μl of 1-bromo-3-chloro-propane were added into the microcentrifuge tube and mixed with the mixture by vortexing for 10 seconds. The microcentrifuge tube was centrifuged at 12000 rpm for 5 minutes. An upper layer aqueous solution was taken out.

420 μl of ethanol was added to the upper layer aqueous solution and mixed with the upper layer aqueous solution slowly to form a mixture. The mixture was loaded into a Favorgen mini column [Favorgen cat#FABRK 001-1], and the Favorgen mini column was centrifuged at 12000 rpm for 30 seconds. A flow-through was re-loaded into the Favorgen mini column, and the Favorgen mini column was centrifuged at 10000 g for 30 seconds. 700 μl of a Wash 2 buffer [Favorgen cat#FABRK 001-1] was added to the Favorgen mini column, and the Favorgen mini column was centrifuged at 12000 rpm for 10 seconds. Then, 80 μl of a DNase solution (10 μl of DNase I+70 μl of RDD buffer, Qiagen #79254) was loaded into the Favorgen mini column and left standing for 15 minutes. 700 μl of 75% ethanol was added to the Favorgen mini column, and the Favorgen mini column was centrifuged at 12000 rpm for 1 minute. The Favorgen mini column was centrifuged at 12000 rpm for 1 minute to dry.

70 μl of RNase-free water was loaded into the Favorgen mini column and left standing for 2 minutes, and then the Favorgen mini column was centrifuged at 12000 rpm for 30 seconds. After that, a flow-through was re-loaded into the Favorgen mini column, and the Favorgen mini column was centrifuged at 12000 rpm for 30 seconds to obtain a final flow-through containing RNA.

Finally, a ratio of the spectral absorbance at 260 nm and 280 nm (A260/280) of the final flow-through was measured by a NANODROP® 1000.

The results of the spectral absorbance measurement were: 260/280=1.6; 260/230=0.8; RNA yield=1.22 μg.

Example 2

Deparaffinization:

A slice of a formalin-fixed paraffin-embedded lung cancer tissue biopsy sample (tissue area: about 1 $cm^2$; thickness: 10 μm) was placed into a microcentrifuge tube. 600 μl of 2,6-dimethyl-2,4,6-octatriene (Allo-ocimene), 194 μl of RNase-free water, 6.3 μl of 1 M Tris-HCl (pH 8.0) and 4.2 μl of 0.5 M EDTA (pH 8.0) were added into the microcentrifuge tube and violently mixed with the sample for 10 seconds. Next, the microcentrifuge tube was placed under a temperature of 50 for shaking horizontally for 5 minutes. The microcentrifuge tube was centrifuged at 12000 rpm for 3 minutes. Then, 500 μl of an upper layer liquid in the microcentrifuge tube was removed. After that, 600 μl of 2,6-dimethyl-2,4,6-octatriene was added into the microcentrifuge tube again and mixed with the remaining liquid by vortexing for 10 seconds. Afterward, the microcentrifuge tube was centrifuged at 12000 rpm for 3 minutes. Finally, 600 μl of an upper layer liquid in the microcentrifuge tube was removed to leave a lower liquid containing a deparaffinized tissue.

RNA Extraction 5.5 μl of 20% SDS and 8 μl of proteinase K [Qiagen #19131, NT$ 17.2/8 μl] were added into the microcentrifuge tube mentioned above which contained the lower liquid containing the deparaffinized tissue and mixed with the lower liquid by vortexing for 10 seconds to form a mixture. The microcentrifuge tube was placed under a temperature of 50° C. for shaking horizontally at 80 rpm for 3 hours. 70 μl of a FARB buffer [Favorgen cat#FABRK 001-1] and 400 μl of 1-bromo-3-chloro-propane were added into the microcentrifuge tube and mixed with the mixture by vortexing for 10 seconds. The microcentrifuge tube was centrifuged at 12000 rpm for 5 minutes. An upper layer aqueous solution was taken out.

420 μl of ethanol was added to the upper layer aqueous solution and mixed with the upper layer aqueous solution slowly to form a mixture. The mixture was loaded into a Favorgen mini column [Favorgen cat#FABRK 001-1], and the Favorgen mini column was centrifuged at 12000 rpm for 30 seconds. A flow-through was re-loaded into the Favorgen mini column, and the Favorgen mini column was centrifuged at 10000 g for 30 seconds. 700 μl of a Wash 2 buffer [Favorgen cat#FABRK 001-1] was added to the Favorgen mini column, and the Favorgen mini column was centrifuged at 12000 rpm for 10 seconds. Then, 80 μl of a DNase solution (10 μl of DNase I+70 μl of RDD buffer, Qiagen #79254) was loaded into the Favorgen mini column and left standing for 15 minutes. 700 μl of 75% ethanol was added to the Favorgen mini column, and the Favorgen mini column was centrifuged at 12000 rpm for 1 minute, and then this step was repeated one time. The Favorgen mini column was centrifuged at 12000 rpm for 1 minute to dry.

70 μl of RNase-free water was loaded into the Favorgen mini column, and then the Favorgen mini column was centrifuged at 12000 rpm for 30 seconds. After that, a flow-through was re-loaded into the Favorgen mini column, and the Favorgen mini column was centrifuged at 12000 rpm for 30 seconds to obtain a final flow-through containing RNA.

Finally, a ratio of the spectral absorbance at 260 nm and 280 nm (A260/280) of the final flow-through was measured by a NANODROP® 1000.

The results of the spectral absorbance measurement were: 260/280=1.89; 260/230=0.8; RNA yield=1.24 μg.

Example 3

Deparaffinization:

10 slices of a formalin-fixed paraffin-embedded lung cancer tissue needle biopsy sample (16 G core needle biopsy) (tissue area: about 5-7 cm$^2$/slice; thickness: 5 μm/slice) were placed into a microcentrifuge tube. 200 μl of xylene and 185 μl of an aqueous solution (30 mM Tris-HCl, pH 8.0, 10 mM EDTA, pH 8.0) were added into the microcentrifuge tube and mixed with the samples by vortexing for 5 seconds to form a mixture. Next, the microcentrifuge tube was centrifuged at 12000 rpm for 1 minute. Finally, an upper layer liquid in the microcentrifuge tube was removed to leave a lower liquid containing a deparaffinized tissue.

DNA Extraction

15 μl of 20% SDS and 10 μl of proteinase K [Qiagen #19131] were added into the microcentrifuge tube mentioned above which contained the lower liquid containing the deparaffinized tissue and mixed with the lower liquid by vortexing for 10 seconds to form a mixture. The microcentrifuge tube was placed under a temperature of 50° C. for rotational shaking at 15 rpm for 3 hours. 130 μl of RLT buffer (Qiagen RNEASY® Mini Kit) was added into the microcentrifuge tube and mixed with the mixture by vortexing for 10 seconds. Then, the microcentrifuge tube was centrifuged at 12000 rpm for 3 minutes. After that, the aqueous solution was taken out from the microcentrifuge tube, and a white precipitate was discarded.

The aqueous solution mentioned above was loaded into a Favorgen micro column (silica column), and the Favorgen micro column was centrifuged at 12000 rpm for 30 seconds. A flow-through generated from the centrifugal step was retained for a subsequent RNA extraction.

Next, 500 μl of 75% ethanol was added to the Favorgen micro column, and the Favorgen micro column was centrifuged at 12000 rpm for 10 seconds, and then this step was repeated one time. The Favorgen micro column was centrifuged at 12000 rpm for 1 minute to dry.

10 μl of RNase-free water was loaded into the Favorgen micro column, and then the Favorgen micro column was centrifuged at 12000 rpm for 30 seconds. After that, a flow-through was re-loaded into the Favorgen micro column, and the Favorgen micro column was centrifuged at 12000 rpm for 30 seconds to obtain a final flow-through containing DNA.

Finally, a ratio of the spectral absorbance at 260 nm and 280 nm (A260/280) of the final flow-through was measured by a NANODROP® 1000.

The results of the spectral absorbance measurement were: 260/280=2.02; 260/230=1.60; DNA yield=86.3 ng.

RNA Extraction

457 μA of 100% ethanol was added to the retained flow-through mentioned above and slowly mixed with the flow-through to form a mixture. The mixture was loaded into a Favorgen micro column, and the Favorgen micro column was centrifuged at 12000 rpm for 30 seconds. A flow-through was re-loaded into the Favorgen micro column, and the Favorgen micro column was centrifuged at 10000 g for 30 seconds. 500 μl of a Wash 2 buffer [Favorgen cat#FABRK 001-1] was added to the Favorgen micro column, and the Favorgen micro column was centrifuged at 12000 rpm for 10 seconds. Then, 24 μl of a DNase solution (3 μl of DNase I 2 0+21 μl of RDD buffer, Qiagen #79254) was loaded into the Favorgen micro column and left standing for 15 minutes. 500 μl of 75% ethanol was added to the Favorgen micro column, and the Favorgen micro column was centrifuged at 12000 rpm for 10 seconds, and then this step was repeated one time. The Favorgen micro column was centrifuged at 12000 rpm for 1 minute to dry.

10 μl of RNase-free water was loaded into the Favorgen micro column, and the Favorgen micro column was centrifuged at 12000 rpm for 30 seconds. After that, a flow-through was re-loaded into the Favorgen micro column, and the Favorgen micro column was centrifuged at 12000 rpm for 30 seconds to obtain a final flow-through containing RNA.

Finally, a ratio of the spectral absorbance at 260 nm and 280 nm (A260/280) of the final flow-through was measured by a NANODROP® 1000.

The results of the spectral absorbance measurement were: 260/280=1.85; 260/230=1.13; RNA yield=183.4 ng.

The spectral absorbance value of the nucleic acid extracted in Example 1, Example 2 and Example 3 are listed in Table 1.

TABLE 1

The spectral absorbance value of the nucleic acid extracted in Example 1, Example 2 and Example 3

| | RNA 260/280 | RNA 260/230 | RNA yield (μg) | DNA 260/280 | DNA 260/230 | DNA yield (μg) |
| --- | --- | --- | --- | --- | --- | --- |
| Example 1 | 1.6 | 0.8 | 1.22 | | | |
| Example 2 | 1.89 | 0.8 | 1.24 | | | |
| Example 3 | 1.85 | 1.13 | 0.183 | 2.02 | 1.60 | 0.086 |

Example 4

The comparison of nucleic acid yields and the gene chip analysis results of the nucleic acid samples obtained from the conventional deparaffinizing method and the deparaffinizing method of the invention.

1. Tissue Source

Each tube contained 5 slices of a formalin-fixed paraffin-embedded human non-small cell lung cancer tissue biopsy sample (thickness: 5 μm/slice). B1 tubes: tissue cross-sectional area of the sample was about 2×2.5 mm$^2$/slice; B2 tubes: tissue cross-sectional area of the sample was about 2.5×3 mm$^2$/slice; B3 tubes: tissue cross-sectional area of the sample was about 3×3 mm$^2$/slice.

2. Deparaffinizing Method

A. Conventional Deparaffinizing Method (1) 200 μl of 100% xylene was added into a microcentrifuge tube containing the sample in a fume hood and violently mixed with the sample by vortexing for 10 seconds to form a mixture. The microcentrifuge tube was placed in oven at 50 for 3 minutes. If the paraffin of the sample was not completely dissolved, this step was repeated again.

(2) After violently vortexing the microcentrifuge tube for 10 seconds, the microcentrifuge tube was centrifuged at 12000 rpm for 3 minutes at room temperature.

(3) The solution in the microcentrifuge tube was carefully removed.

(4) The microcentrifuge tube was centrifuged at 12000 rpm for 2 minutes, and then remained solution was removed and a precipitate was kept.

(5) 200 μl of 100% ethanol was added into the microcentrifuge tube, and the microcentrifuge tube was flicked slightly to mix the precipitate with the ethanol.

(6) The microcentrifuge tube was centrifuged at 12000 rpm for 2 minutes in a room temperature centrifuge.

(7) The solution (containing xylene and ethanol) was taken out and discarded, and a precipitate was kept.

(8) Steps (5)-(7) were repeated again.

(9) The microcentrifuge tube containing the precipitate was placed in a fume hood at room temperature for 15 minutes to evaporate the remaining ethanol.

(10) 175 μl of RNase-free water, 6 μl of 1 M Tris-HCl (pH 8.0) and 4 μl of 0.5 M EDTA (pH 8.0), 15 μl of 20% SDS and 10 μl of proteinase K [Qiagen #19131] were added into the microcentrifuge tube containing the precipitate and mixed with the precipitate by vortexing 10 seconds to form a mixture. The microcentrifuge tube was placed under a temperature of 50° C. for rotational shaking at 15 rpm for 3 hours.

(11) The DNA and RNA extraction steps described in the following were performed.

B. Deparaffinizing Method of the Invention (1) 175 μl of RNase-free water, 6 μl of 1 M Tris-HCl (pH 8.0) and 4 μl of 0.5 M EDTA (pH 8.0) were added into a microcentrifuge tube containing the sample. 200 μl of xylene was added into the microcentrifuge tube in a fume hood and mixed with the solutions mentioned above and the sample by vortexing for 5 seconds. Then the microcentrifuge tube was centrifuged at 12000 rpm for 1 minute. Next, the upper layer was discarded and a lower layer solution was kept (it was not needed to completely remove the upper layer solution, as the volume of the upper layer solution was less than 20 μl.)

(2) 15 μl of 20% SDS and 10 μl of proteinase K were added into the microcentrifuge tube in a fume hood and mixed with the lower layer solution by vortexing for 10 seconds to form a mixture. Then, the microcentrifuge tube was placed under a temperature of 50° C. for rotational shaking at 15 rpm for 3 hours.

(3) The DNA and RNA extraction steps described in the following were performed.

3. DNA and RNA Extractions (1) After the conventional deparaffinizing method and the deparaffinizing method of the invention were completely performed, a 130 μl RLT buffer (Qiagen RNEASY® Mini Kit) was added into the mixture of the microcentrifuge tube of the conventional deparaffinizing method and the mixture of the microcentrifuge tube of the deparaffinizing method of the invention mentioned above, respectively and mixed with the mixture of the microcentrifuge tube of the conventional deparaffinizing method and the mixture of the microcentrifuge tube of the deparaffinizing method of the invention mentioned above by vortexing for 10 seconds, respectively. Both the microcentrifuge tube of the conventional deparaffinizing method and the microcentrifuge tube of the deparaffinizing method of the invention were centrifuged at 12000 rpm for 3 minutes. The aqueous solution in the microcentrifuge tube of the conventional deparaffinizing method and that of the microcentrifuge tube of the deparaffinizing method of the invention were taken out. Both the two aqueous solutions were subjected to the following steps.

(2) The aqueous solution was loaded into and passed through a Favorgen micro column (marked as a DNA column), and the DNA column was centrifuged at 12000 rpm for 30 seconds to generate a flow-through.

(3) 1.5 times volume of the flow-through of an absolute ethanol was added to the flow-through and slowly mixed with the flow-through to form a mixture.

(4) The mixture was loaded into a new Favorgen micro column (marked as a RNA column), and the RNA column was centrifuged at 12000 rpm for 30 seconds. A flow-through was re-loaded into the RNA column, and the RNA column was centrifuged at 12000 rpm for 30 seconds, and then a flow-through therefrom was discarded.

(5) 500 μl of a Wash 2 buffer [Favorgen cat#FABRK 001-1] was added to the RNA column, and the RNA column was centrifuged at 12000 rpm for 10 seconds.

(6) 16 μA of a DNase solution (2 μl of DNase I+14 μl of RDD buffer, Qiagen #79254) was loaded into the RNA column and left standing for 15 minutes.

(7) 500 μl of 75% ethanol was added to the DNA column and the RNA column, respectively. The DNA column and the RNA column were centrifuged at 12000 rpm for 1 minute. This step was repeated one time.

(8) The DNA column and the RNA column were centrifuged at 12000 rpm for 1 minute to dry. The DNA column and the RNA column were placed into a new 1.5 ml microcentrifuge, respectively.

(9) 10 μl of RNase-free water was loaded into the DNA column and the RNA column, respectively. The DNA column and the RNA column were centrifuged at 12000 rpm for 30 seconds. A flow-through from the DNA column and the RNA column were re-loaded into the DNA column and the RNA column, respectively. After that, the DNA column and the RNA column were centrifuged again to obtain a flow-through from the DNA column and the RNA column, respectively.

(10) A ratio of the spectral absorbance at 260 nm and 280 nm (A260/280) of the flow-through from the DNA column and that of the flow-through from RNA column were measured by a NANODROP® 1000, respectively, and the nucleic acid yields were calculated according to the measurement results. The results are shown in Table 1.

4. Gene Chip Analysis

Two gene chip (Whole-Genome DASL® Assay) (Illumina cat# DA-903-0024) experiments were performed by using 200 ng of B3 tube RNA samples obtained by the conventional deparaffinizing method and the deparaffinizing method of the invention, respectively, according to the manufacturer's manual.

5. Results

A. DNA and RNA Yields

FIG. 1 shows nucleic acid yields obtained by using a conventional deparaffinizing method and the deparaffinizing method of the invention, respectively (B1 tubes: tissue cross-sectional area of the sample was about 2×2.5 mm$^2$/slice; B2 tubes: tissue cross-sectional area of the sample was about 2.5×3 mm$^2$/slice; and B3 tubes: tissue cross-sectional area of the sample was about 3×3 mm$^2$/slice). Each data was obtained from a triplicate experiment. According to the results shown in FIG. 1, it is clearly shown that the deparaffinizing method of the invention is capable of raising the DNA and RNA yields by reducing the tissues loss.

B. Gene Chip Analysis

Figure 2:
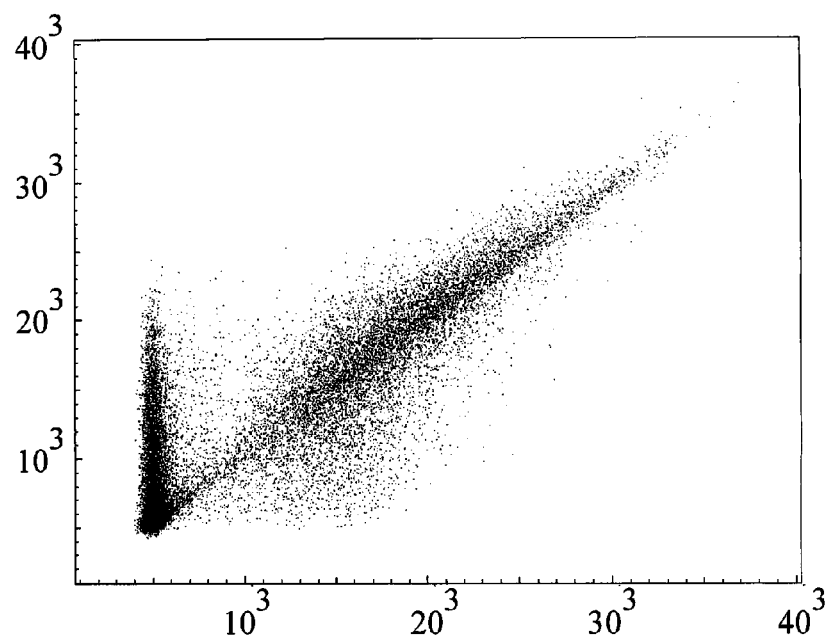
FIG. 2 is a scatter plot of gene chip analysis results between RNA samples obtained by using the conventional deparaffinizing method and by the deparaffinizing method of the invention.

FIG. 2 is a scatter plot of gene chip analysis results between RNA samples obtained by using the conventional deparaffinizing method and by the deparaffinizing method of the invention. (the X axis represents gene chip signal intensity measured from RNA sample of the conventional deparaffinizing method; and the Y axis represents gene chip signal intensity measured from RNA sample of the deparaffinizing method of the invention). According to FIG. 2, it is clearly shown that the gene signals detected from RNA sample of the deparaffinizing method of the invention was more than the gene signals detected from the RNA sample of the conventional deparaffinizing method.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for deparaffinizing a formalin-fixed paraffin-embedded tissue, comprising:
    providing a formalin-fixed paraffin-embedded tissue sample;
    mixing the formalin-fixed paraffin-embedded tissue sample with an organic solvent and water or with an organic solvent and an aqueous solution to form a mixture, wherein a density of the organic solvent is less than that of the water or the aqueous solution, and the organic solvent is immiscible with the water or the aqueous solution; and
    separating the mixture into an organic solution layer and an aqueous solution layer, wherein a paraffin dissolved from the formalin-fixed paraffin-embedded tissue sample is in the organic solution layer and a deparaffinized tissue from the formalin-fixed paraffin-embedded tissue sample is in the aqueous solution layer and/or an interlayer between the organic solution layer and the aqueous solution layer,
    wherein a step of repeatedly washing the formalin-fixed paraffin-embedded tissue sample with ethanol or the aqueous solution thereof is not included in the method for deparaffinizing a formalin-fixed paraffin-embedded tissue.

2. The method for deparaffinizing a formalin-fixed paraffin-embedded tissue as claimed in claim 1, wherein a method for separating the mixture into the organic solution layer and the aqueous solution layer comprises performing a centrifugal process to the mixture.

3. The method for deparaffinizing a formalin-fixed paraffin-embedded tissue as claimed in claim 1, further comprising after the step of separating the mixture into the organic solution layer and the aqueous solution layer, removing the organic solution layer.

4. The method for deparaffinizing a formalin-fixed paraffin-embedded tissue as claimed in claim 3, further comprising:
    after the step of removing the organic solution layer, adding the organic solvent into the aqueous solution layer;
    mixing the organic solvent with the aqueous solution layer to form a second mixture; and
    separating the second mixture into a second organic solution layer and a second aqueous solution layer.

5. The method for deparaffinizing a formalin-fixed paraffin-embedded tissue as claimed in claim 4, wherein a method for separating the second mixture into the second organic solution layer and the second aqueous solution layer comprises performing a centrifugal process to the second mixture.

6. The method for deparaffinizing a formalin-fixed paraffin-embedded tissue as claimed in claim 4, further comprising after the step of separating the second mixture into the second organic solution layer and the second aqueous solution layer, removing the second organic solution layer.

7. The method for deparaffinizing a formalin-fixed paraffin-embedded tissue as claimed in claim 1, wherein the organic solvent comprises a non-polar hydrocarbon or a mixture of hydrocarbons.

8. The method for deparaffinizing a formalin-fixed paraffin-embedded tissue as claimed in claim 1, wherein the organic solvent comprises an alkylbenzene.

9. The method for deparaffinizing a formalin-fixed paraffin-embedded tissue as claimed in claim 8, wherein the alkylbenzene is xylene or toluene.

10. The method for deparaffinizing a formalin-fixed paraffin-embedded tissue as claimed in claim 1, wherein the organic solvent comprises an aliphatic hydrocarbon, a terpene, a petroleum distillate or an isoparaffinic hydrocarbon.

11. The method for deparaffinizing a formalin-fixed paraffin-embedded tissue as claimed in claim 10, wherein the terpene is 2,6-dimethyl-2,4,6-octatriene.

12. The method for deparaffinizing a formalin-fixed paraffin-embedded tissue as claimed in claim 1, wherein content of the aqueous solution comprises water, Tris-HCl and EDTA.

* * * * *